(12) United States Patent
Fernandez Lara et al.

(10) Patent No.: US 10,816,427 B2
(45) Date of Patent: Oct. 27, 2020

(54) INTEGRATED FUEL COMPOSITION AND PRESSURE SENSOR

(71) Applicant: Ford Global Technologies, LLC, Dearborn, MI (US)

(72) Inventors: Arturo Sebastian Fernandez Lara, Naucalpan (MX); Manuel Iván Calderón Delgado, Cuautitlán Izcalli (MX); Enrique Lopez Hernandez, Toluca (MX); Diego Cabrera Padilla, Mexico City (MX); Said Alan Sánchez Martínez, Mexico City (MX)

(73) Assignee: Ford Global Technologies, LLC, Dearborn, MI (US)

( * ) Notice: Subject to any disclaimer, the term of this patent is extended or adjusted under 35 U.S.C. 154(b) by 247 days.

(21) Appl. No.: 15/975,029

(22) Filed: May 9, 2018

(65) Prior Publication Data

US 2019/0346324 A1 Nov. 14, 2019

(51) Int. Cl.
*G01L 19/00* (2006.01)
*F02D 19/06* (2006.01)
*F02D 19/08* (2006.01)
*G01N 27/22* (2006.01)
*G01N 33/22* (2006.01)
*G01L 9/12* (2006.01)

(52) U.S. Cl.
CPC ...... *G01L 19/0092* (2013.01); *F02D 19/0631* (2013.01); *F02D 19/0636* (2013.01); *F02D 19/084* (2013.01); *F02D 19/088* (2013.01); *G01L 9/12* (2013.01); *G01N 27/228* (2013.01); *G01N 33/22* (2013.01); *F02D 2200/0604* (2013.01); *F02D 2200/0612* (2013.01)

(58) Field of Classification Search
CPC ..... G01L 19/0092; G01L 9/12; F02D 19/063; F02D 19/0636; F02D 19/084; F02D 19/088; G01N 27/228; G01N 33/22
USPC .................................................. 73/61.61, 780
See application file for complete search history.

(56) References Cited

U.S. PATENT DOCUMENTS

| | | | |
|---|---|---|---|
| 3,524,116 A * | 8/1970 | Bray | H01G 4/04 361/284 |
| 5,044,344 A | 9/1991 | Tuckey et al. | |
| 5,124,654 A * | 6/1992 | Scheid | G01N 27/07 123/494 |
| 5,151,660 A | 9/1992 | Powers et al. | |
| 5,182,942 A | 2/1993 | Hartel et al. | |
| 6,578,416 B1 | 6/2003 | Vogel et al. | |
| 9,164,009 B2 | 10/2015 | Mouchel La Fosse et al. | |
| 9,470,594 B2 | 10/2016 | Cornwell et al. | |

(Continued)

FOREIGN PATENT DOCUMENTS

| | | | | |
|---|---|---|---|---|
| EP | 2042719 A2 | | 4/2009 | |
| GB | 2205654 A * | 12/1988 | | ........... G01L 9/0005 |
| WO | WO-03042653 A2 * | 5/2003 | | ........... G01N 27/226 |

*Primary Examiner* — Nimeshkumar D Patel
*Assistant Examiner* — Jean F Morello
(74) *Attorney, Agent, or Firm* — Geoffrey Brumbaugh; McCoy Russell LLP

(57) ABSTRACT

Methods and systems are provided for an integrated fuel composition-pressure sensor. In one example, the integrated sensor may include a set of cylindrical capacitors and a set of plate capacitors with a common capacitor element shared between the sets. A composition of fuel may be determined from the set of cylindrical capacitors and a pressure of fuel may be determined from the set of plate capacitors.

18 Claims, 8 Drawing Sheets

(56) References Cited

U.S. PATENT DOCUMENTS

| | | |
|---|---|---|
| 2005/0040834 A1 | 2/2005 | Sanchez et al. |
| 2010/0007360 A1* | 1/2010 | Kaess .................. G01N 27/226 324/672 |
| 2010/0301877 A1* | 12/2010 | Paterson .............. G01N 33/246 324/664 |

* cited by examiner

INTEGRATED FUEL COMPOSITION AND PRESSURE SENSOR

FIELD

The present description relates generally to an electronic device for determining a fuel composition and a fuel pressure in a fuel line.

BACKGROUND/SUMMARY

Flexible fuel vehicles (FFVs) are an alternative to conventional gasoline-driven vehicles and include an internal combustion engine to combust mixtures of gasoline and a secondary fuel, such as methanol, ethanol, propanol, or other alcohols and octane improvers. Fuel blends incorporating ethanol are particularly popular due to a derivation of ethanol from biomass, with various feedstocks available from agriculture. A flexible fuel engine may be adapted to burn fuel mixtures of 0-100% ethanol, thereby reducing gasoline consumption and emission of undesirable byproducts of gasoline combustion.

In order to adjust engine operations to accommodate changes in fuel composition, a powertrain control module (PCM) may undergo a learning process. The PCM's ability to effectively diagnose changes in fueling conditions may be dependent on reception of accurate signals to provide parameters as a basis for calculations. For example, to determine suitable air-fuel ratios at combustion chambers of the engine, the PCM may utilize an estimate or measurement of the fuel composition (e.g., percentage of ethanol) and a fuel pressure to determine an amount of fuel to be injected.

The PCM may obtain such information from sensors configured to measure pressure and fuel composition. In one approach described by Tuckey et al. in U.S. Pat. No. 5,044,344, a fuel delivery system of an engine includes a fuel delivery module configured with a sensor that is responsive to fuel alcohol concentration. The fuel delivery module also includes a pressure sensor coupled to the fuel delivery line to measure a fuel delivery pressure. Signals from the pressure sensor and alcohol concentration sensor are sent to an amplifier that communicates with a fuel pump that drives fuel flow to the engine.

However, the inventors herein have recognized potential issues with such systems. As one example, the use of separate sensors to measure the pressure and composition of fuel combusted in the engine adds complexity, costs, weight, and packaging space of the fuel system. In addition, the sensors disclosed in U.S. Pat. No. 5,044,344 are positioned in the fuel tank and may not account for pressure losses in the fuel line with distance from the fuel tank. As fuel flows through the fuel line before reaching the combustion chambers, a final delivery pressure may differ significantly from pressures measured at the tank and lead to poor combustion efficiency.

In one example, the issues described above may be addressed by an integrated fuel composition and pressure sensor, comprising a set of cylindrical capacitors concentrically arranged and spaced apart from one another, where the set of cylindrical capacitors are adapted to receive a flow of fluid axially through each capacitor of the set of cylindrical capacitors, and a set of plate capacitors spaced apart from one another, where a common capacitor element is shared between the set of cylindrical capacitors and set of plate capacitors. In this way, fuel pressure and fuel composition of fuel may be measured by a single sensor that may be positioned proximal to combustion chambers of the engine.

As one example, the electronic device includes a first set of ceramic plates for determining the fuel pressure and a second set of concentric cylindrical ceramic plates for determining fuel composition of fuel. A shell of an outer cylindrical plate of the second set of ceramic plates may be shared between the two sets of ceramic plates and used in both measurements. A capacitance may be calculated between each of the first and second sets of plates based on a voltage potential. A permittivity of the fuel flowing through the electronic device may be determined by the second set of cylindrical ceramic plates and used to calculate a percentage of ethanol in the fuel. The permittivity may also be used to calculate a capacitance of the first set of ceramic plates which, along with an adjustment to account for a change in fluid pressure due to flow through the electronic device, may determine the fuel pressure.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 3-5 are shown approximately to scale.

DETAILED DESCRIPTION

Figure 2:
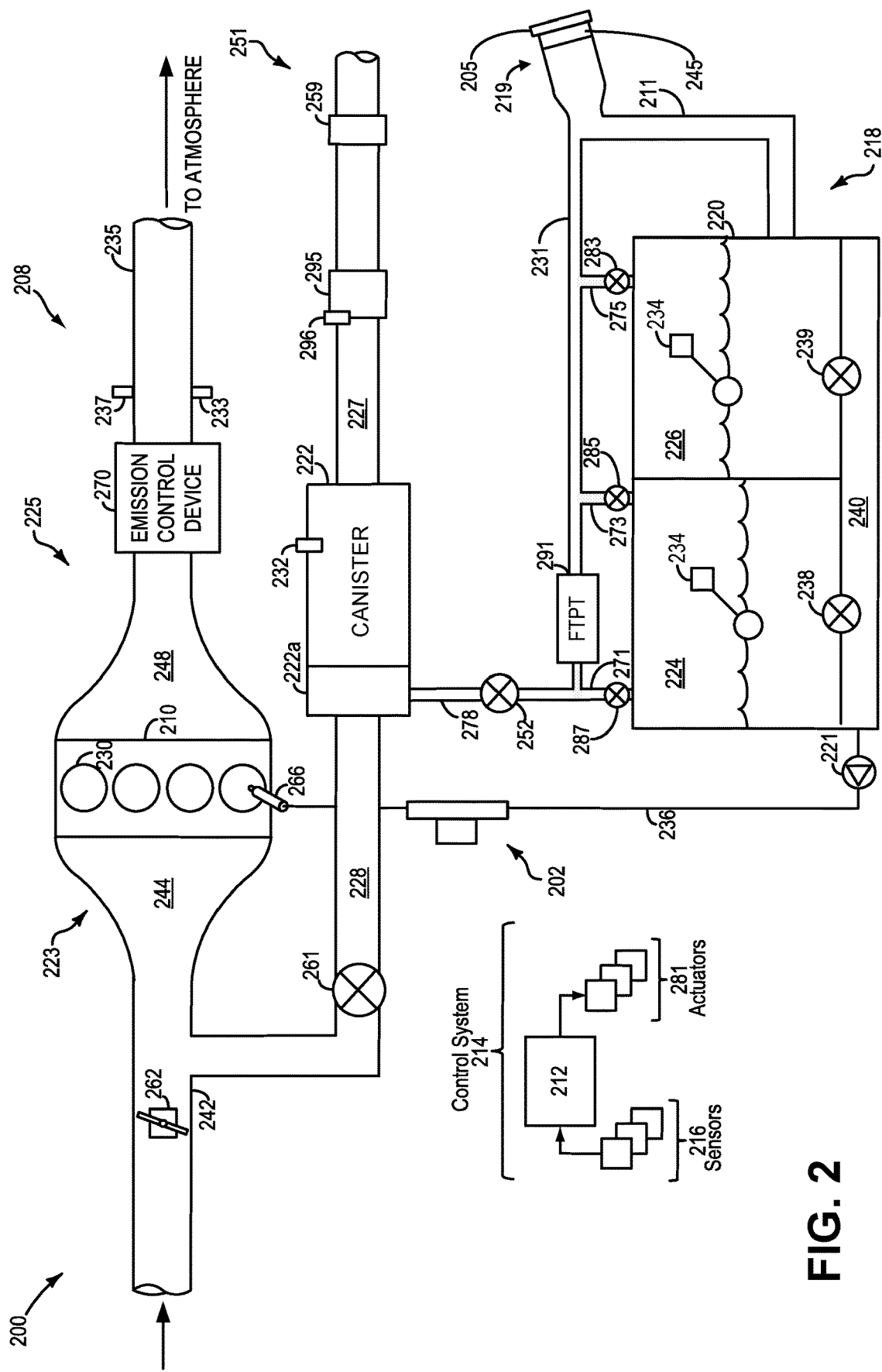
FIG. 2 shows an example of an engine system configured with an integrated composition-pressure sensor arranged in a fuel line.
Figure 3:
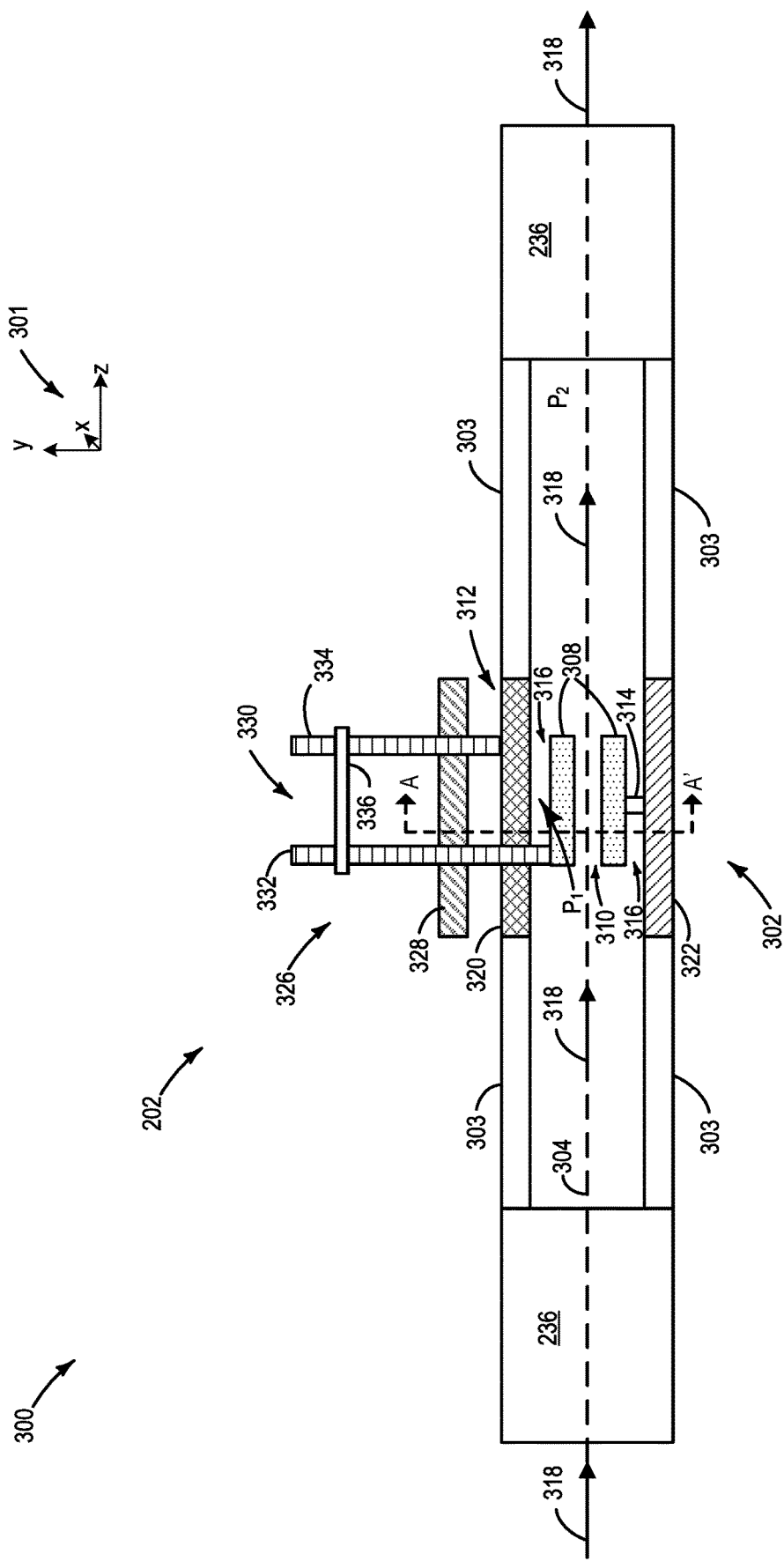
FIG. 3 shows an example of an integrated composition-pressure sensor adapted to measure fuel pressure and fuel composition of fuel.
Figure 5:
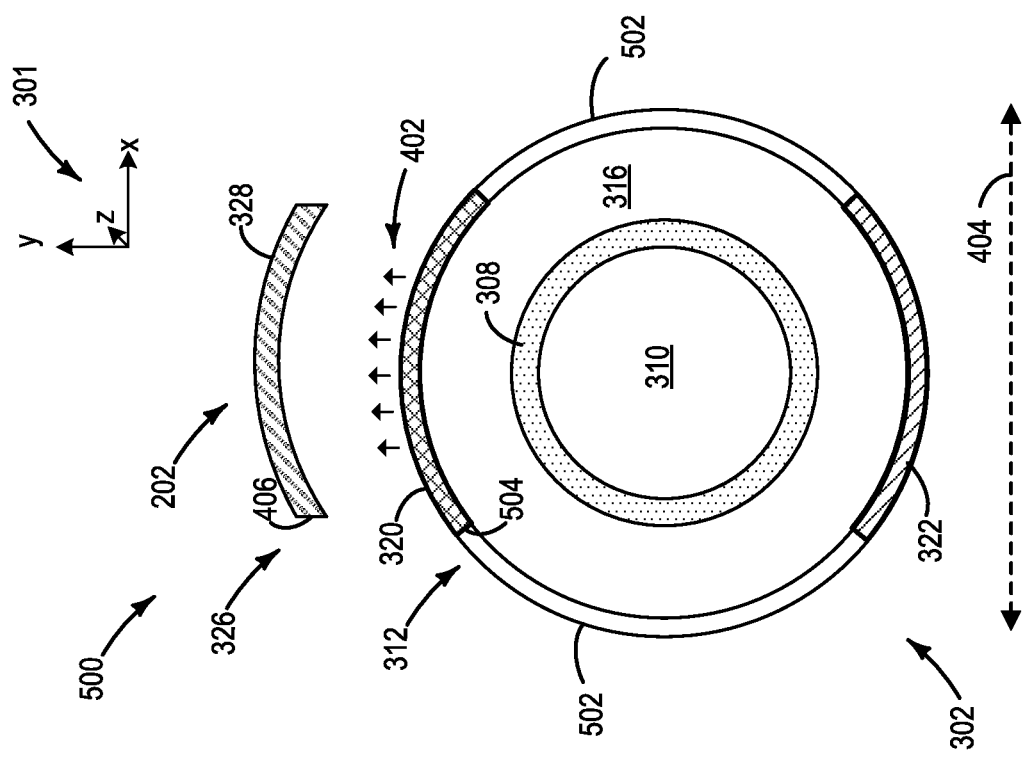
FIG. 5 shows a second cross-section of an example of an integrated composition-pressure sensor.
Figure 4:
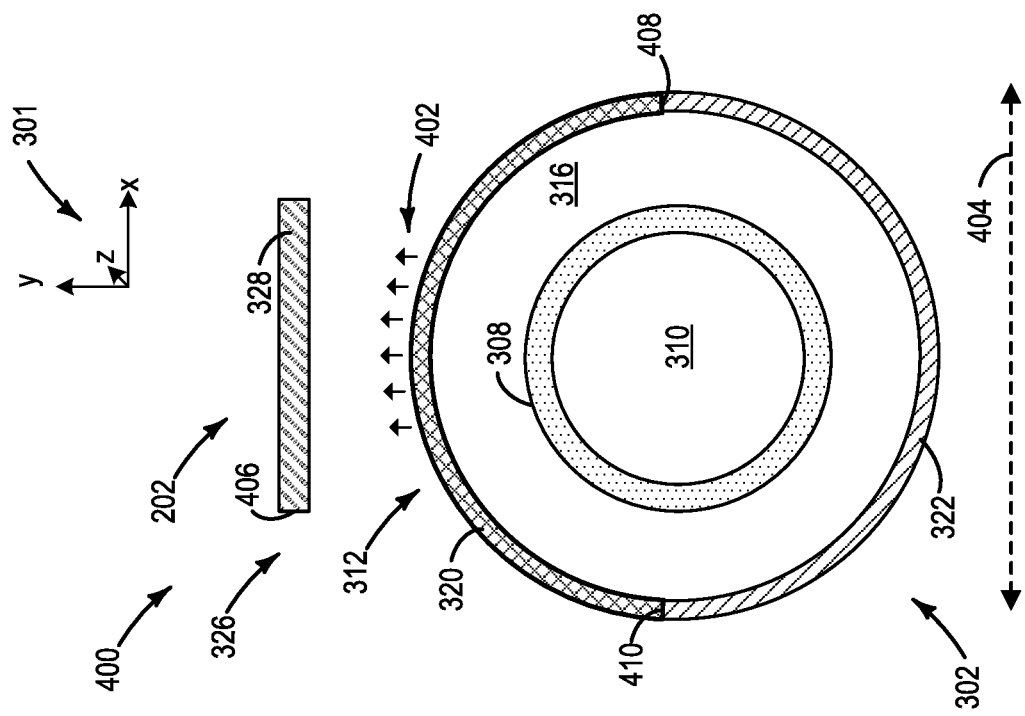
FIG. 4 shows a first cross-section of an example of an integrated composition-pressure sensor.
Figure 6:
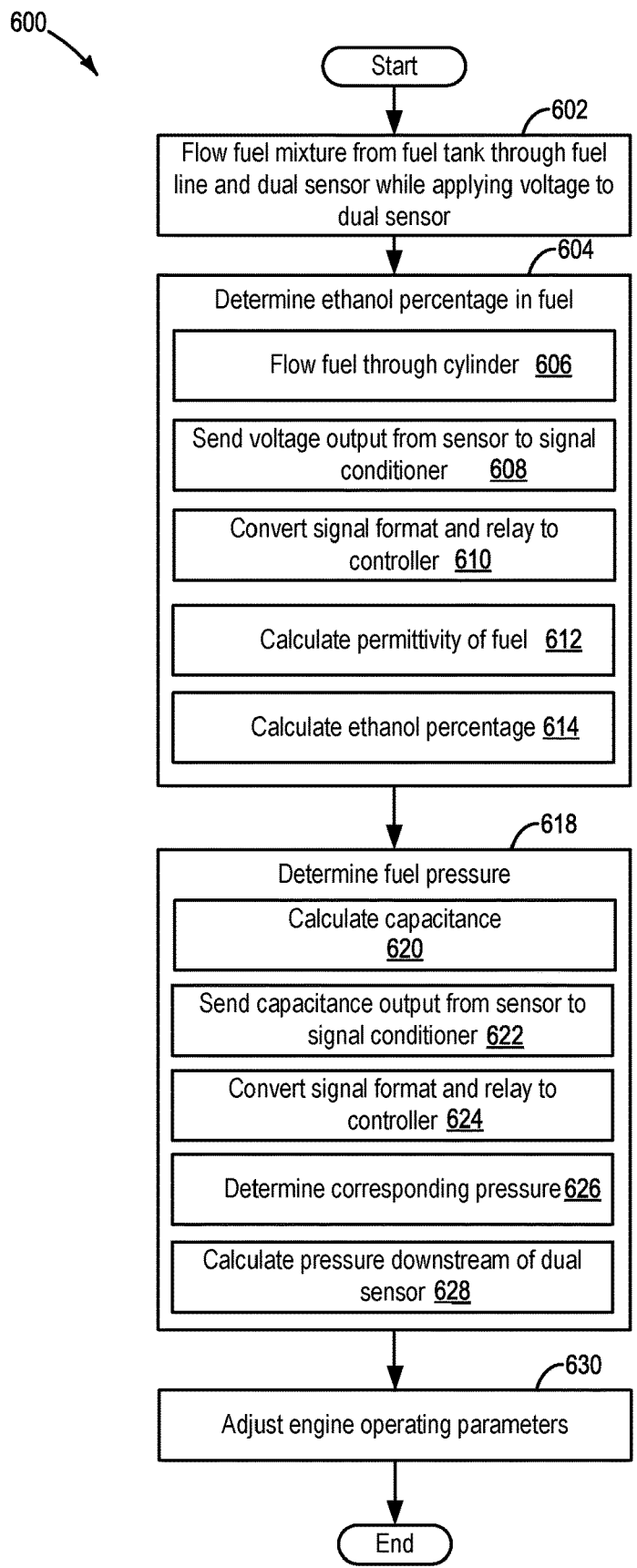
FIG. 6 shows an example of a method for measuring fuel pressure and fuel composition of fuel via an integrated composition-pressure sensor.

The following description relates to a device for measuring both fuel composition and fuel pressure of a fuel combusted in an engine. The device may be included in an engine system of a vehicle and in particular, positioned in a fuel line between a fuel tank and cylinders of an engine. An example of a vehicle including such an engine system is given in FIG. 1 and an example of an engine system configured with the device is shown in FIG. 2. The device may be an integrated sensor for measuring both a pressure and composition of fuel combusted at the engine. The integrated sensor may include sensing elements including integrated capacitance plates and concentrically arranged capacitance cylinders, as illustrated in a side cut-away view of the integrated composition-pressure sensor in FIG. 3. Cross-sections of the integrated composition-pressure sensor, providing a view perpendicular to the view of FIG. 3 are shown in FIGS. 4 and 5, illustrating variations in a geometry of a second cylinder of the integrated composition-pressure sensor. FIG. 6 is an example of a method for operating the integrated composition-pressure sensor to obtain a composition of a fuel blend flowing from the fuel tank to the engine. Variables that may be used to calculate the fuel composition and fuel pressure as described in the method of FIG. 6 are represented in schematic diagrams of cylindrical capacitors used to determine the fuel composition and capacitor plates used in combination with the cylindrical capacitors to determine the fuel pressure in FIGS. 7, 8, and 10. A schematic diagram depicted in FIG. 9 illustrates a transmission of electronic signals from the integrated composition-pressure sensor to an engine controller where the determined fuel composition and fuel pressure may be used to adjust engine operations such as spark, fuel injection, and crankshaft timing.

FIGS. 1-5 and 7-10 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Figure 1:
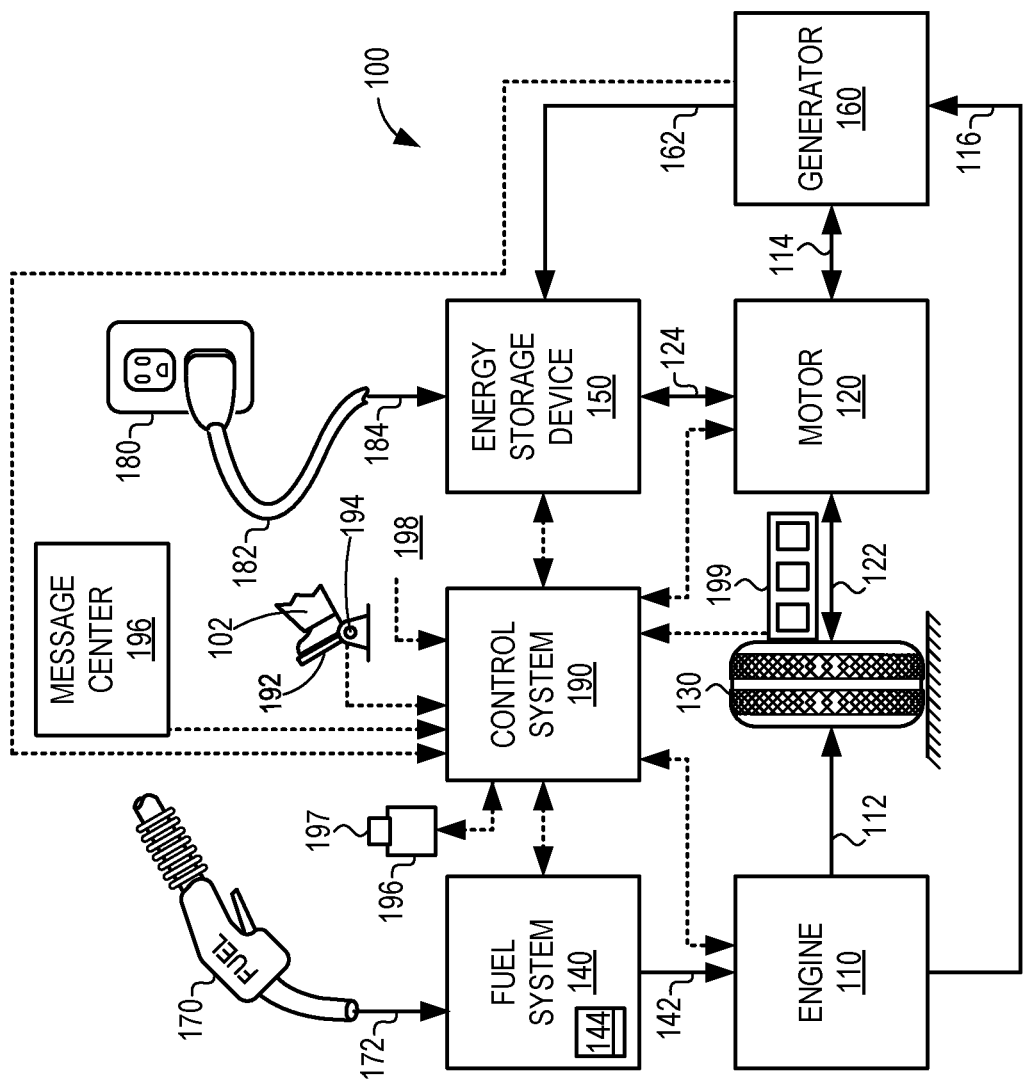
FIG. 1 shows a schematic diagram of a vehicle in which an integrated composition-pressure sensor may be used to measure a fuel composition and fuel pressure of fuel.

Turning now to the figures, FIG. 1 illustrates an example vehicle propulsion system 100. Vehicle propulsion system 100 includes a fuel burning engine 110 and a motor 120. As a non-limiting example, engine 110 comprises an internal combustion engine and motor 120 comprises an electric motor. Motor 120 may be configured to utilize or consume a different energy source than engine 110. For example, engine 110 may consume a liquid fuel (e.g. gasoline, ethanol, or a gasoline-ethanol blend) to produce an engine output while motor 120 may consume electrical energy to produce a motor output. As such, a vehicle with propulsion system 100 may be referred to as a hybrid electric vehicle (HEV) and a vehicle that combusts fuel mixtures may be referred to as a flexible fuel vehicle (FFV).

Vehicle propulsion system 100 may utilize a variety of different operational modes depending on operating conditions encountered by the vehicle propulsion system. Some of these modes may enable engine 110 to be maintained in an off state (e.g., set to a deactivated state) where combustion of fuel at the engine is discontinued. For example, under select operating conditions, motor 120 may propel the vehicle via drive wheel 130 as indicated by arrow 122 while engine 110 is deactivated.

During other operating conditions, engine 110 may be set to a deactivated state (as described above) while motor 120 may be operated to charge energy storage device 150. For example, motor 120 may receive wheel torque from drive wheel 130 as indicated by arrow 122 where the motor may convert the kinetic energy of the vehicle to electrical energy for storage at energy storage device 150 as indicated by arrow 124. This operation may be referred to as regenerative braking of the vehicle. Thus, motor 120 can provide a generator function in some embodiments. However, in other embodiments, generator 160 may instead receive wheel torque from drive wheel 130, where the generator may convert the kinetic energy of the vehicle to electrical energy for storage at energy storage device 150 as indicated by arrow 162.

During still other operating conditions, engine 110 may be operated by combusting fuel received from fuel system 140 as indicated by arrow 142. For example, engine 110 may be operated to propel the vehicle via drive wheel 130 as indicated by arrow 112 while motor 120 is deactivated. During other operating conditions, both engine 110 and motor 120 may each be operated to propel the vehicle via drive wheel 130 as indicated by arrows 112 and 122, respectively. A configuration where both the engine and the motor may selectively propel the vehicle may be referred to as a parallel type vehicle propulsion system. Note that in some embodiments, motor 120 may propel the vehicle via a first set of drive wheels and engine 110 may propel the vehicle via a second set of drive wheels.

In other embodiments, vehicle propulsion system 100 may be configured as a series type vehicle propulsion system, whereby the engine does not directly propel the drive wheels. Rather, engine 110 may be operated to power motor 120, which may in turn propel the vehicle via drive wheel 130 as indicated by arrow 122. For example, during select operating conditions, engine 110 may drive generator 160, which may in turn supply electrical energy to one or more of motor 120 as indicated by arrow 114 or energy storage device 150 as indicated by arrow 162. As another example, engine 110 may be operated to drive motor 120 which may in turn provide a generator function to convert the engine output to electrical energy, where the electrical energy may be stored at energy storage device 150 for later use by the motor. The vehicle propulsion system may also be configured to transition between two or more of the operating modes described above depending on operating conditions.

Fuel system 140 may include one or more fuel storage tanks 144 for storing fuel on-board the vehicle. For example, fuel tank 144 may store one or more liquid fuels, including but not limited to: gasoline, diesel, and alcohol fuels. In some examples, the fuel may be stored on-board the vehicle as a blend of two or more different fuels. For example, fuel tank 144 may be configured to store a blend of gasoline and ethanol (e.g. E10, E85, etc.) or a blend of gasoline and methanol (e.g. M10, M85, etc.), whereby these fuels or fuel blends may be delivered to engine 110 as indicated by arrow 142. Still other suitable fuels or fuel blends may be supplied to engine 110, where they may be combusted at the engine to produce an engine output. The engine output may be utilized to propel the vehicle as indicated by arrow 112 or to recharge energy storage device 150 via motor 120 or generator 160.

In some embodiments, energy storage device 150 may be configured to store electrical energy that may be supplied to other electrical loads residing on-board the vehicle (other than the motor), including cabin heating and air conditioning, engine starting, headlights, cabin audio and video systems, etc. As a non-limiting example, energy storage device 150 may include one or more batteries and/or capacitors.

Control system 190 may communicate with one or more of engine 110, motor 120, fuel system 140, energy storage device 150, and generator 160. Control system 190 may receive sensory feedback information from one or more of engine 110, motor 120, fuel system 140, energy storage device 150, and generator 160. Further, control system 190 may send control signals to one or more of engine 110, motor 120, fuel system 140, energy storage device 150, and generator 160 responsive to this sensory feedback. Control system 190 may receive an indication of an operator requested output of the vehicle propulsion system from a vehicle operator 102. For example, control system 190 may receive sensory feedback from pedal position sensor 194 which communicates with pedal 192. Pedal 192 may refer schematically to a brake pedal and/or an accelerator pedal.

In other embodiments, electrical transmission cable 182 may be omitted, where electrical energy may be received wirelessly at energy storage device 150 from power source 180. For example, energy storage device 150 may receive electrical energy from power source 180 via one or more of electromagnetic induction, radio waves, and electromagnetic resonance. As such, it should be appreciated that any suitable approach may be used for recharging energy storage device 150 from a power source that does not comprise part of the vehicle. In this way, motor 120 may propel the vehicle by utilizing an energy source other than the fuel utilized by engine 110. Fuel system 140 may periodically receive fuel from a fuel source residing external to the vehicle. As a non-limiting example, vehicle propulsion system 100 may be refueled by receiving fuel via a fuel dispensing device 170 as indicated by arrow 172. In some embodiments, fuel tank 144 may be configured to store the fuel received from fuel dispensing device 170 until it is supplied to engine 110 for combustion. In some embodiments, control system 190 may receive an indication of the level of fuel stored at fuel tank 144 via a fuel level sensor. The level of fuel stored at fuel tank 144 (e.g. as identified by the fuel level sensor) may be communicated to the vehicle operator, for example, via a fuel gauge or indication lamp indicated at 196. Furthermore, the fuel system 140 may include one or more sensors for detecting a fuel composition when more than one fuel type is used for combustion, as well as for measuring a fuel pressure.

FIG. 2 shows a schematic depiction of a vehicle system 200. The vehicle system 200 includes an engine system 208 coupled to an emissions control system 251 and a fuel system 218. Emission control system 251 includes a fuel vapor container or canister 222 which may be used to capture and store fuel vapors. In some examples, vehicle system 200 may be a flexible fuel vehicle system (FFV) and/or a hybrid electric vehicle system.

The engine system 208 may include an engine 210 having a plurality of cylinders 230. The engine 210 includes an engine intake 223 and an engine exhaust 225. The engine intake 223 includes a throttle 262 fluidly coupled to an engine intake manifold 244 via an intake passage 242. The engine exhaust 225 includes an exhaust manifold 248 leading to an exhaust passage 235 that routes exhaust gas to the atmosphere. The engine exhaust 225 may include one or more emission control devices 270, which may be mounted in a close-coupled position in the exhaust. One or more emission control devices may include a three-way catalyst, lean NOx trap, diesel or gasoline particulate filter, oxidation catalyst, etc. In some examples, the exhaust manifold 248 may be configured with exhaust gas recirculation, coupling the exhaust manifold to the intake passage 242 upstream of the engine intake 223 to mix burnt gas with intake air prior to re-combustion (not shown in FIG. 2). It will be appreciated that other components may be included in the engine such as a variety of valves and sensors.

Fuel system 218 may include a fuel tank 220 coupled to a fuel pump system 221. The fuel pump system 221 may include one or more pumps for pressurizing fuel delivered to the injectors of engine 210, such as the example injector 266 shown. While only a single injector 266 is shown, additional injectors are provided for each cylinder. It will be appreciated that fuel system 218 may be a return-less fuel system, a return fuel system, or various other types of fuel system. Fuel tank 220 may hold a plurality of fuel blends, including fuel with a range of alcohol concentrations, such as various gasoline-ethanol blends, including E10, E85, gasoline, etc., and combinations thereof.

For example, fuel tank 220 is shown in FIG. 2 with a first inner compartment 224 and a second inner compartment 226. A first type of fuel, such as gasoline, may be stored in the first inner compartment 224, and a second type of fuel, such as ethanol, may be stored in the second inner compartment 226. Fuel level sensors 234 located in the first inner compartment 224 and the second inner compartment 226 of fuel tank 220 may provide an indication of the fuel levels ("Fuel Level Input") to controller 212. As depicted, fuel level sensors 234 may comprise a float connected to a variable resistor. Alternatively, other types of fuel level sensors may be used. Valves 238 and 239 may control flow of fuel from the first and second inner compartments 224, 226, into a mixing compartment 240, where the two fuel types may be mixed in a desired ratio before being pumped through into a fuel line 236 by the fuel pump 221.

Fuel line 236 couples the fuel tank 220 to the engine 210. Efficient combustion and peak torque derived from combustion may depend on engine operations such as spark timing, fuel injection timing, intake and exhaust valve timing, shifting at the transmission, etc. Adjustment of the engine operations to provide a desirable engine performance may be conducted according to a measured fuel composition and fuel pressure. The fuel composition and fuel pressure may be determined by an integrated sensor 202, arranged inline in the fuel line 236 and positioned closer to the engine 210 than the fuel tank 220. The integrated sensor 202 may be a single device configured to measure both a pressure and composition of the fuel in the fuel line 236. The measurements may be obtained by electrical outputs of shared elements of the integrated sensor 202 to determine individual values of pressure and composition. In this way, fuel flowing through fuel line 236 may flow directly through (e.g., through a center or central portion of) the integrated sensor 202. The integrated sensor 202 may output signals (e.g., two signals from two different electrodes, as explained further below) to the controller 212 which may then be used by the controller 212 to determine (e.g., calculate) a percentage of ethanol in the fuel, for example, and a pressure of the fuel in the fuel line 236 between the integrated sensor 202 and the engine 210. Components and operation of the integrated sensor 202 are elaborated below in descriptions of FIGS. 3-8.

Vapors generated in fuel system 218 may be routed to an evaporative emissions control system 251 which includes a fuel vapor canister 222 via vapor recovery line 231, before being purged to the engine intake 223. Vapor recovery line 231 may be coupled to fuel tank 220 via one or more conduits and may include one or more valves for isolating the fuel tank during certain conditions. For example, vapor recovery line 231 may be coupled to fuel tank 220 via one or more or a combination of conduits 271, 273, and 275.

Further, in some examples, one or more fuel tank vent valves are in conduits 271, 273, or 275. Among other functions, fuel tank vent valves may allow a fuel vapor canister of the emissions control system to be maintained at a low pressure or vacuum without increasing the fuel evaporation rate from the tank (which would otherwise occur if the fuel tank pressure were lowered). For example, conduit 271 may include a grade vent valve (GVV) 287, conduit 273 may include a fill limit venting valve (FLVV) 285, and conduit 275 may include a grade vent valve (GVV) 283. Further, in some examples, recovery line 231 may be coupled to a fuel filler system 219. In some examples, fuel filler system may include a fuel cap 205 for sealing off the fuel filler system from the atmosphere. Refueling system 219 is coupled to fuel tank 220 via a fuel filler pipe or neck 211.

Further, refueling system 219 may include refueling lock 245. In some embodiments, refueling lock 245 may be a fuel cap locking mechanism. The fuel cap locking mechanism may be configured to automatically lock the fuel cap in a closed position so that the fuel cap cannot be opened. For example, the fuel cap 205 may remain locked via refueling lock 245 while pressure or vacuum in the fuel tank is greater than a threshold. In response to a refuel request, e.g., a vehicle operator initiated request, the fuel tank may be depressurized and the fuel cap unlocked after the pressure or vacuum in the fuel tank falls below a threshold. The fuel cap locking mechanism may alternatively be a latch or clutch, which, when engaged, prevents the removal of the fuel cap. The latch or clutch may be electrically locked, for example, by a solenoid, or may be mechanically locked, for example, by a pressure diaphragm.

In some embodiments, refueling lock 245 may be a filler pipe valve located at a mouth of fuel filler pipe 211. In such embodiments, refueling lock 245 may not prevent the removal of fuel cap 205. Rather, refueling lock 245 may prevent the insertion of a refueling pump into fuel filler pipe 211. The filler pipe valve may be electrically locked, for example by a solenoid, or mechanically locked, for example by a pressure diaphragm. In other embodiments, refueling lock may be a refueling door lock or locked using an electrical mechanism.

Emissions control system 251 may include one or more emissions control devices, such as one or more fuel vapor canisters 222 filled with an appropriate adsorbent, the canisters are configured to temporarily trap fuel vapors (including vaporized hydrocarbons) during fuel tank refilling operations and "running loss" (that is, fuel vaporized during vehicle operation). In one example, the adsorbent used is activated charcoal. Emissions control system 251 may further include a canister ventilation path or vent line 227 which may route gases out of the canister 222 to the atmosphere when storing, or trapping, fuel vapors from fuel system 218.

Canister 222 may include a buffer 222a (or buffer region), each of the canister and the buffer comprising the adsorbent. As shown, the volume of buffer 222a may be smaller than (e.g., a fraction of) the volume of canister 222. The adsorbent in the buffer 222a may be same as, or different from, the adsorbent in the canister (e.g., both may include charcoal). Buffer 222a may be positioned within canister 222 such that during canister loading, fuel tank vapors are first adsorbed within the buffer, and then when the buffer is saturated, further fuel tank vapors are adsorbed in the canister. In comparison, during canister purging, fuel vapors are first desorbed from the canister (e.g., to a threshold amount) before being desorbed from the buffer. In other words, loading and unloading of the buffer is not linear with the loading and unloading of the canister. As such, the effect of the canister buffer is to dampen any fuel vapor spikes flowing from the fuel tank to the canister, thereby reducing the possibility of any fuel vapor spikes going to the engine. One or more temperature sensors 232 may be coupled to and/or within canister 222. As fuel vapor is adsorbed by the adsorbent in the canister, heat is generated (heat of adsorption). Likewise, as fuel vapor is desorbed by the adsorbent in the canister, heat is consumed. In this way, the adsorption and desorption of fuel vapor by the canister may be monitored and estimated based on temperature changes within the canister.

Vent line 227 may also allow fresh air to be drawn into canister 222 when purging stored fuel vapors from fuel system 218 to engine intake 223 via purge line 228 and purge valve 261. For example, purge valve 261 may be normally closed but may be opened during certain conditions so that vacuum from engine intake manifold 244 is provided to the fuel vapor canister for purging. In some examples, vent line 227 may include an air filter 259 disposed therein upstream of a canister 222.

In some examples, the flow of air and vapors between canister 222 and the atmosphere may be regulated by a canister vent valve coupled within vent line 227. When included, the canister vent valve may be a normally open valve, so that fuel tank isolation valve 252 (FTIV) may control venting of fuel tank 220 with the atmosphere. FTIV 252 may be positioned between the fuel tank and the fuel vapor canister within conduit 278. FTIV 252 may be a normally closed valve, that when opened, allows for the venting of fuel vapors from fuel tank 220 to canister 222. Fuel vapors may then be vented to atmosphere, or purged to engine intake system 223 via canister purge valve 261.

Fuel system 218 may be operated by controller 212 in a plurality of modes by selective adjustment of the various valves and solenoids. For example, the fuel system may be operated in a fuel vapor storage mode (e g., during a fuel tank refueling operation and with the engine not running), wherein the controller 212 may open isolation valve 252 while closing canister purge valve (CPV) 261 to direct refueling vapors into canister 222 while preventing fuel vapors from being directed into the intake manifold.

As another example, the fuel system may be operated in a refueling mode (e.g., when fuel tank refueling is requested by a vehicle operator), wherein the controller 212 may open isolation valve 252, while maintaining canister purge valve 261 closed, to depressurize the fuel tank before allowing enabling fuel to be added therein. As such, isolation valve 252 may be kept open during the refueling operation to allow refueling vapors to be stored in the canister. After refueling is completed, the isolation valve may be closed.

As yet another example, the fuel system may be operated in a canister purging mode (e.g., after an emission control device light-off temperature has been attained and with the engine running), wherein the controller 212 may open canister purge valve 261 while closing isolation valve 252. Herein, the vacuum generated by the intake manifold of the operating engine may be used to draw fresh air through vent 27 and through fuel vapor canister 22 to purge the stored fuel vapors into intake manifold 44. In this mode, the purged fuel vapors from the canister are combusted in the engine. The purging may be continued until the stored fuel vapor amount in the canister is below a threshold.

Controller 212 may comprise a portion of a control system 214. Control system 214 is shown receiving information from a plurality of sensors 216 (various examples of which are described herein) and sending control signals to a plurality of actuators 281 (various examples of which are described herein). As one example, sensors 216 may include exhaust gas sensor 237 located upstream of the emission control device, temperature sensor 233, fuel tank pressure sensor (FTPT) 291, canister temperature sensor 243, and integrated sensor 202. Other sensors such as pressure, temperature, air/fuel ratio, and composition sensors may be coupled to various locations in the vehicle system 200. As another example, the actuators may include fuel injector 266, throttle 262, fuel tank isolation valve 253, pump 292, and refueling lock 245. The control system 214 may include a controller 212. The controller may receive input data from the various sensors, process the input data, and trigger the actuators in response to the processed input data based on instructions or code programmed therein (e.g., programmed and stored on a memory of the controller) corresponding to one or more routines. An example control routine for determining the fuel composition and fuel pressure from integrated sensor 202 is described herein with regard to FIG. 6.

As described above, engine performance may be increased by adjusting engine operations in response to a determined composition and pressure of a fuel blend in a FFV. The fuel composition and fuel pressure may be estimated based on outputs (e.g., measurement signals) from an integrated sensor, such as the integrated sensor 202 of FIG. 2. For example, the integrated sensor 202 may relay signals indicating capacitances generated by components of the sensor which are due to changing ethanol percentage and/or pressure of the fuel flowing through the integrated sensor. The capacitance is a ratio of a change in electric charge in a system to a corresponding change in an electric potential of the system and may be a function of a geometry of the integrated sensor and permittivity of the fuel flowing through the integrated sensor.

A cut-away side view 300 of the integrated sensor 202 is shown in FIG. 3. A set of reference axes 301 are provided, indicating a y-axis, x-axis, and z-axis. The integrated sensor 202 has a first section 302 that is arranged inline with the fuel line 236 so that fuel flowing through the fuel line also flows through the first section 302 of the integrated sensor 202. At least a portion of the first section 302 is arranged entirely within an interior of a flow passage 303 of the sensor 202. The first section 302 may have a central axis 304 that is also a central axis 304 of the fuel line 236 and includes a set of cylindrical capacitors comprising at least two concentrically arranged cylinders. The cylinders may be formed from ceramic or from other conductive materials. As shown in FIG. 3, the first section 302 includes a first cylinder 308, shown as two planar plates in the cut-away side view 300, that is aligned so that an inner passage 310 of the first cylinder 308 is centered along the central axis 304 and a central axis of the first cylinder 308 is coaxial with the central axis 304. The first cylinder 308 may be surrounded by a second, larger (e.g., larger diameter) cylinder 312, also shown as two planar plates in the cut-away side view 300. Each of the first cylinder 308 (which may be referred to as an inner cylinder) and the second cylinder 312 (which may be referred to as an outer cylinder, where inner/outer are relative to the central axis 304) are annular and have an inner diameter and outer diameter, which a thickness of each cylinder defined between respective inner and outer diameters. For example, the second cylinder 312 may have an outer diameter that is substantially equal to an outer diameter of the fuel line 236 and the flow passage 303 of the integrated sensor 202, and an inner diameter that is substantially equal to an inner diameter of the fuel line 236 and the flow passage 303. In other examples, however, the outer diameter and inner diameter of the second cylinder 312 may differ from the outer diameter and inner diameter of the fuel line 236.

The first cylinder 308 may be enclosed by and spaced away from the second cylinder 312 so that an outer surface of the first cylinder 308 does not contact an inner surface of the second cylinder 312. A position of the first cylinder 308, centered within the second cylinder 312, may be anchored by a rigid stem 314, formed from a non-conductive material, connecting the first cylinder 308 to the second cylinder 312. An outer flow passage 316 is formed between the outer surface of the first cylinder 308 and the inner surface of the second cylinder 312. Fuel flowing through the fuel line 236 along a direction indicated by arrow 318, which is parallel with the central axis 304, may flow continuously through the inner passage 310 of the first cylinder 308, as well as through the outer passage 316. The fuel contacts both the inner and outer surfaces of the first cylinder 308 and the inner surface of the second cylinder 312.

The second cylinder 312 may comprise a first shell 320 and a second shell 322. In one example, the first shell 320 and the second shell 322 may be coupled together to form a continuous cylindrical surface (forming a complete cylinder), as shown in a first cross-section 400 of the integrated sensor 202 in FIG. 4. The first cross-section 400 is taken along A-A' in FIG. 3. In other words, each the first shell 320 and the second shell 322 may form half of the second cylinder 312. The edges 408 of the first shell 320 and the edges 410 of the second shell 322 may be connected by sections of a material of the fuel line 236. In other examples, however, each of the first shell 320 and the second shell 322 may be less than half of the second cylinder 312, the remainder of the cylinder formed by panels of a material forming the flow passage 303. As an example, as shown in a second cross-section 500 of the integrated sensor 202 in FIG. 5, the first shell 320 and the second shell 322 may each comprise a quarter of the annular cross-section of the second cylinder 312. The second cross-section 500 is also taken along A-A' in FIG. 3. The first shell 320 and the second shell 322 may be connected by panels 502, also formed from the material of the flow passage 303. While the first shell 320 and second shell 322 are shown in FIGS. 3-5 to be of similar dimensions, other examples of the integrated sensor 202 may include the second cylinder 312 with the first shell 320 smaller (e.g., narrow, thinner, and/or shorter) than the second shell 322, or the first shell 320 larger (e.g., wider, thicker, and/or longer) than the second shell 322.

The first shell 320 may be configured to bend or deflect when experiencing an outward (e.g., away from the central axis 304) force from a pressure of the fuel flowing through the outer passage 316. A curvature of the first shell 320 may increase slightly due to the pressure in an outwards direction, as indicated by arrows 402 shown in FIGS. 4 and 5. As the first shell 320 may be formed from ceramic and may be brittle and resistant to bending, the increase in curvature of the first shell may be relatively small. Alternatively, the first shell 320 may be adapted to shift radially outward in response to increased pressure in the outer passage 316 without varying the curvature while remaining connected, such as to the panels 502 in FIG. 5. The second shell 322 may respond similarly to changes in pressure of fuel flowing through the second cylinder 312 or may be configured to maintain a position of the second shell 322 regardless of pressure.

Returning to FIG. 3, the integrated sensor 300 may have a second section 326, in addition to the first section 302, that protrudes outwards, away from the central axis 304, and is mostly positioned external to, e.g., outside of, the flow passage 303 and also outside of the flow path of the fuel line 236. The second section 326 may comprise a parallel set of capacitance plates with first shell 320 of the second cylinder 312 forming one plate of the set of parallel capacitance plates and an external plate 328, e.g., external to a path of fuel flow, forming a second plate of the set of parallel capacitance plates. The external plate 328 may also be formed from ceramic or some other type of conductive material. The external plate 328 may be positioned above the first shell 320 of the second cylinder 312, with respect to the y-axis, and spaced away from the first shell 320 by a distance that may vary as the first shell 320 bends in response to an increase in pressure from fuel flowing through the cylindrical capacitance plates. Said another way, the external plate 328 is positioned outside of the first shell 320, with respect to central axis 304 and an outer (e.g., external) wall of flow passage 303. The external plate 328 may be configured to be static and, unlike the first shell 320, does not bend in response to a change in the pressure of the fuel.

The external plate 328 may be configured to be a same length as the first shell 320 of the second cylinder 312, as shown in FIG. 3, the length defined along the z-axis. In alternate embodiments, the length of the first shell 320 and external plate 328 may be different. In one example, the external plate 328 may be planar, as shown in FIG. 4 and may have a width, defined along the x-axis, that is wider or narrower (as shown in FIG. 4) than an outer diameter 404 of the second cylinder 312. In another example, as shown in FIG. 5, the external plate 328 may be curved, with a curvature matching the base, unbent curvature of the first shell 320 of the second cylinder 312. The curved external plate 328 may also have a width that is narrower or wider than the outer diameter 404 of the second cylinder 312. In addition, a thickness of the external plate 328, defined along the y-axis, may be equal to, thinner, or thicker than the thickness of the first shell 320 of the second cylinder 312.

The second section 326 of the integrated sensor 202 may also include an electronic device 330, as shown in FIG. 3, to transmit electronic signals from the integrated sensor 202 to an engine control system, such as the controller 212 of engine control system 214 of FIG. 2. The electronic device 330 may be formed from a conductive material, such as a metal or a composite, and comprise a first electrode 332 and a second electrode 334, both the first and second electrodes 332, 334 arranged perpendicular to the central axis 304. The first electrode 332 and the second electrode 334 may be linked by a crossbar 336 that maintains positions of the first electrode 332 and the second electrode 334. The crossbar 336 may be coaxial with the central axis 304 and spaced away from and above the external plate 328.

The first electrode 332 of the electronic device 330 may extend down from a height above the external plate 332, through the external plate 328 and through the first shell 320 of the second cylinder 312 to contact the outer surface of the first cylinder 308. The external plate 328 and the first shell 320 may be adapted with apertures to accommodate insertion of the first electrode 332. The portion of the first electrode 332 between the inner surface of the second cylinder 312 and the outer surface of the first cylinder 308 may be immersed in fuel. The first electrode 332 may alternatively extend along a side edge of the external plate 328, e.g., side edge 406 shown in FIGS. 4-5, and along a side edge 504 shown in FIG. 5 of the first shell 320 of the second cylinder 312 if the external plate 328 and the first shell 320 have widths that allow an adjacent positioning of the first electrode 332 while remaining aligned, along the y-axis, with the first cylinder 308.

The second electrode 334 may be aligned parallel to and spaced away from the first electrode 332 by a distance less than a width (defined along the z-axis) of the crossbar 336. The second electrode 334 may extend down from a height equal to a height of the first electrode 332 above the external plate 332, either penetrating through the thickness of the external plate 328 or along the side edge 406 of the external plate 328. Unlike the first electrode 332, the second electrode may contact an outer surface of the first shell 320 of the second cylinder 312 but not extend through the first shell 320 and not contact the first cylinder 308. The first and second electrodes 332, 334 thereby transmit electronic signals from different sets of capacitance plates, the first electrode 332 relaying an electronic signal generated from a capacitance difference between the two cylinders of the set of cylindrical capacitors (e.g., first cylinder 308 and second cylinder 312) and the second electrode 334 relaying an electronic signal generated from a capacitance difference between the two plates of the set of plate capacitors (e.g., external plate 328 and first shell 320). In this way, the sensor 202 may output two electronic signals, with the first shell 320 of the second cylinder 312 being used by the sensor to produce each of the two electronic signals.

The integrated sensor 202 may be enclosed within an outer housing, as shown in FIG. 2 to provide a barrier between the second section 326 of the integrated sensor 202 and other objects, such as other engine components. The aperture in the first shell 320 of the second cylinder 312 or one of the panels 502 (as shown in FIG. 5), through which the first electrode 332 may be inserted may be sealed so that fuel from the outer passage 316 of the integrated sensor 202 may not flow through the aperture into the encased second section 326 of the integrated sensor 202.

In this way, an integrated sensor may be used to determine a fuel composition (e.g., percentage of ethanol in a gasoline/ethanol blend) and a fuel pressure of fuel flowing in a fuel line upstream of engine cylinders of an engine. The integrated sensor, comprising a set of cylindrical capacitors and a set of plate capacitors that share an element (e.g., the first shell 320 of the second cylinder 312 of FIGS. 3-5), may be connected to an electrical storage device, such as energy storage device 150 of FIG. 1. A potential may be applied to each of the set of cylindrical capacitors and the set of plate capacitors. A potential difference between a first cylinder and a second cylinder, the second cylinder surrounding the first cylinder and spaced away by a distance, may be measured and used to calculate a capacitance of the set of cylindrical capacitors. The capacitance may deviate by an amount, based on the potential difference, from a predetermined capacitance of the set of cylindrical capacitors. The capacitance change of the set of cylindrical capacitors may be converted into an electrical signal, such as a voltage, and sent to an engine controller by the electronic device where a permittivity of the fuel may be determined from the electrical signal and compared to permittivities of gasoline and ethanol. For example, a relative permittivity of gasoline may be 2 and a relative permittivity of ethanol may be 24.3. The calculated permittivity of the fuel may be a value between 2 and 24.3 and a percentage of ethanol in the mixture of gasoline and ethanol may be calculated based on the calculated permittivity value relative to the permittivities of gasoline and ethanol.

The fuel pressure may be determined from the set of plate capacitors. The set of plate capacitors may be spaced apart by a known distance when fuel is stationary or at a low flow rate through the set of cylindrical capacitors. However, when fuel flow increases through the set of cylindrical capacitors, a pressure from the fuel may exert an outwards, e.g., away from a central axis of the cylinders, force on the outermost cylinder of the set of cylindrical capacitors. The outermost cylinder may be adapted to bend outwards in response to the fuel pressure, decreasing the distance between the set of plate capacitors. The change in distance results in a change in capacitance of the set of plate capacitors. A calculation of the change in capacitance of the set of capacitance plates may include a potential difference between the plates as well as the permittivity of the fuel determined from the set of capacitance cylinders. The change in capacitance may be converted to a voltage that is conveyed to the controller. At the controller, a pressure of the fuel in the fuel line within the integrated sensor between an inner cylinder, e.g., the first cylinder 308 of FIGS. 3-5, and a first shell of the outer cylinder, e.g., the first shell 320 of the second cylinder 312 of FIGS. 3-5, may be determined to correspond to the change in capacitance.

The fuel pressure within the integrated sensor, e.g., $P_1$ in FIG. 3, may differ from a fuel pressure downstream of the integrated sensor, e.g., $P_2$ of FIG. 2, between the integrated sensor and the engine, due to the presence of the inner cylinder within the fuel flow path. The interaction of the fuel with the inner cylinder may generate friction, increasing fuel pressure within the integrated sensor compared to the fuel pressure downstream of the integrated sensor. The downstream fuel pressure (upstream of the engine) may be estimated based on a calculated effect on the fuel pressure arising from friction between the fuel and the inner cylinder, providing a pressure of the fuel when the fuel reaches the engine. Fuel pressure and fuel composition of fuel injected into cylinders of the engine are thus measured by a single device (e.g., single electronic sensor) that is arranged proximal to the engine, thereby accounting for changes in fuel pressure along the fuel line. Calculations used to determine the fuel composition and fuel pressure will be elaborated further below in an example of a routine shown in FIG. 6.

An example of a routine 600 for determining a fuel composition and a fuel pressure of fuel from an integrated sensor arranged in a fuel line, between a fuel tank and an engine of a vehicle and proximal to the engine, is provided in FIG. 6. The integrated sensor may include a set of cylindrical capacitors and a set of plate capacitors with a common capacitor element shared between the two sets. An energy storage device may be coupled to the integrated sensor, supplying a voltage to the capacitors of the integrated sensor. The integrated sensor may also comprise an electronic device, such as the electronic device 330 of FIG. 3, to relay signals from the integrated sensor to a controller, such as controller 212 of FIG. 2. Instructions for carrying out method 600 and the rest of the methods included herein may be executed by the controller based on instructions stored on a memory of the controller and in conjunction with signals received from sensors of the engine system, such as the sensors described above with reference to FIG. 2. The controller may employ engine actuators of the engine system to adjust engine operation, according to the methods described below.

At 602, the method includes flowing fuel from the fuel tank to the engine through the fuel line. The fuel may be gasoline, ethanol, or a blend of gasoline and ethanol. Flowing the fuel may include actuating a fuel pump, such as fuel pump 221 of FIG. 2, to pump fuel out of the fuel tank towards the engine. As the integrated sensor is placed inline in the fuel line, the fuel also flows through the integrated sensor. A voltage may be applied to the integrated sensor at 602 by the energy storage device. The controller may command a connection of a circuit to provide a preset voltage to the integrated sensor from which baseline capacitances of the capacitors of the integrated sensor may be obtained based on stationary gasoline or ethanol in the integrated sensor as a dielectric material. A powertrain control module (PCM) may be a component of the controller, computing fuel injection timing based on signals received by the controller.

The fuel composition of the fuel flowing through the fuel line is determined at 604.

Determining the fuel composition may comprise flowing fuel through the set of cylindrical capacitors at 606. The set of cylindrical capacitors includes a first, smaller diameter cylinder aligned so that fuel flows along a length of the first cylinder through an inner passage and an outer passage of the first cylinder. The first cylinder is positioned inside a second cylinder of the set of cylindrical capacitors, as shown by the first cylinder 308 and second cylinder 312 shown in FIGS. 3-5 and 7, and centered within the second cylinder, arranged parallel with the first cylinder. A length of the first cylinder may be less than or equal to a length of the second cylinder. The outer passage of the first cylinder may also be an inner passage of the second cylinder. The second cylinder may be formed from a first shell and a second shell, the first shell arranged above the second shell. The first and second shell may be coupled directly to one another or coupled by panels, such as the panels 502 of FIG. 5, arranged between the first and second shells. In this way, fuel may flow through an interior passage formed by an interior of the first cylinder and an outer passage formed between an outer wall of the first cylinder and an inner wall of the second cylinder (e.g., the outer passage formed in the space that separates the first and second cylinder).

An electronic signal indicating a change in capacitance may be generated by the electronic device when a composition of the fuel changes, e.g., the ethanol percentage decreases or increases. The electronic device may include a first electrode coupled to the set of cylindrical capacitors that relays a capacitance from the set of cylindrical capacitors to a signal conditioner at 608. At 610, the signal conditioner may convert the signal to a format readable by the controller, such as a voltage. Conditioning of the signal may be illustrated in a schematic diagram 900 in FIG. 9. The electronic device of the integrated sensor 202 may send a signal 902 via a first path 904 to a signal conditioner 906. In one example, the signal may be analog and the signal conditioner 906 may be an amplifier that converts the analog signal to a digital signal 908. The signal 908 may be sent to the controller 212.

Figure 7:
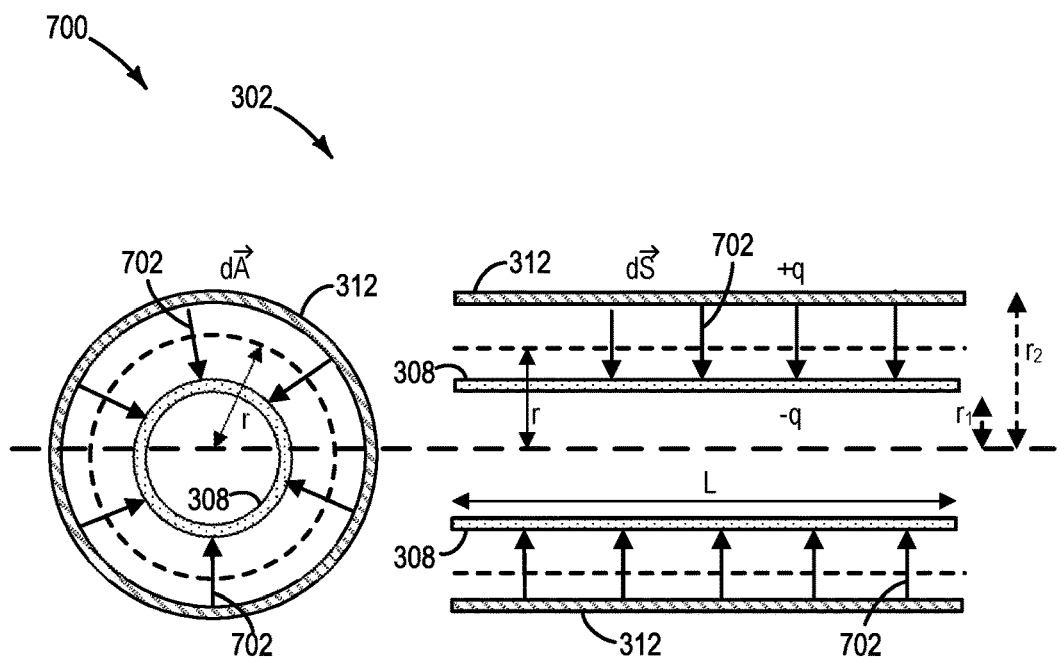
FIG. 7 shows a schematic diagram of a set of cylindrical capacitors and parameters included in a determination of fuel composition.

At 612, the method includes calculating a permittivity of the fuel. Geometrical parameters of the integrated sensor such as, the radii of the first and second cylinders (e.g., $r_1$ and $r_2$ in FIG. 7), an area of a cross section of the set of cylindrical capacitors, volumes of the first and second cylinders, a distance between an inner surface of the second cylinder and outer surface of the first cylinder, and the lengths of the first and second cylinders, may be stored in a memory of the controller and used in the determination of the permittivity. As an example, a schematic diagram 700 of the integrated sensor 202 is shown in FIG. 7, depicting a cross-section of the first section of the integrated sensor 202, taken from a plane perpendicular to the central axis of the first and second cylinders 308, 312 on the left and a cross-section of the first and second cylinders 308, 312 taken along the central axis is shown on the right. An electric field may be generated between the first cylinder 308 and the second cylinder 312, as indicated by arrows 702. From Gauss's Law, a Gaussian surface may be included to describe the electric potential difference using a difference between $r_1$ and $r_2$, a stored electric charge q, and a length L of the first and second cylinders 308, 312, according to, $$\Delta V = \frac{q}{\epsilon 2\pi L} \ln\left(\frac{r_2}{r_1}\right) \quad (1)$$

where $\epsilon$ is a fuel permittivity of the fuel flowing through the integrated sensor.

A capacitance of the first section 302 of the integrated sensor 202 may be measured by the integrated sensor and related to the electric potential difference using the following relationship, $$C = \left|\frac{q}{\Delta V}\right| \quad (2)$$

The electronic device may be configured to measure capacitance and equations (1) and (2) may be combined to determined equation (3), as described below. The measured capacitance may be converted to a voltage output by the signal conditioner and sent to the controller. In one example, the voltage may correspond to the permittivity of the fuel. At the controller, the permittivity may be determined at 612 according to, $$\epsilon = \frac{C \ln\left(\frac{r_2}{r_1}\right)}{2\pi L} \quad (3)$$

Based on value of a relative permittivity of gasoline of $\epsilon \approx 2$ and a relative permittivity of gasoline of $\epsilon \approx 24.3$ stored in the controller's memory, the percentage of ethanol in the fuel blend flowing through the integrated sensor may be inferred at 614 of the method.

Inferring the percentage of ethanol in the fuel blend may include referring to a look-up table describing a relationship of the fuel permittivity to percentage of ethanol. For example, the controller may compare the calculated permittivity as an input to a list of ethanol/gasoline ratios resulting in specific permittivities. A corresponding ethanol percentage may be output based on the permittivity to estimate the fuel composition.

Figure 8:
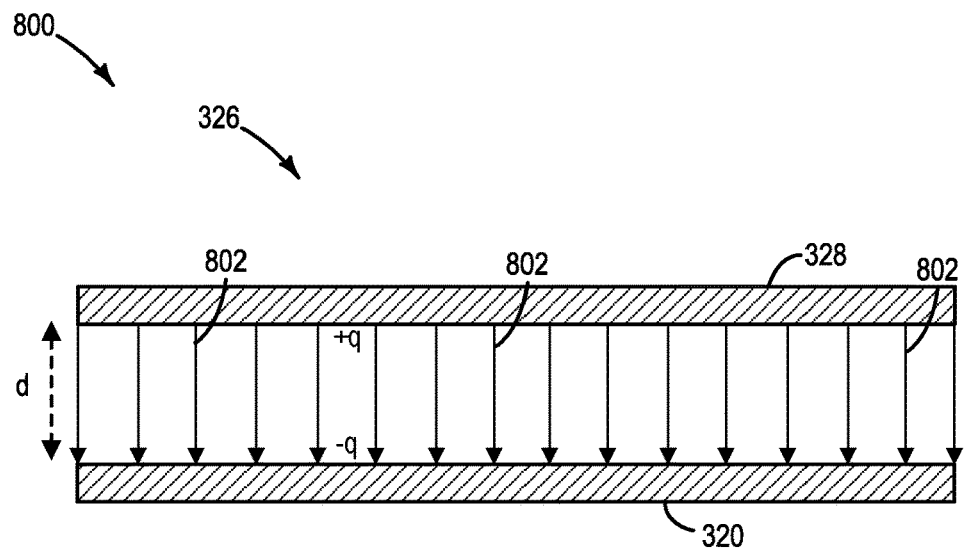
FIG. 8 shows a schematic diagram of a set of capacitor plates and parameters included in a determination of fuel composition.
Figure 9:
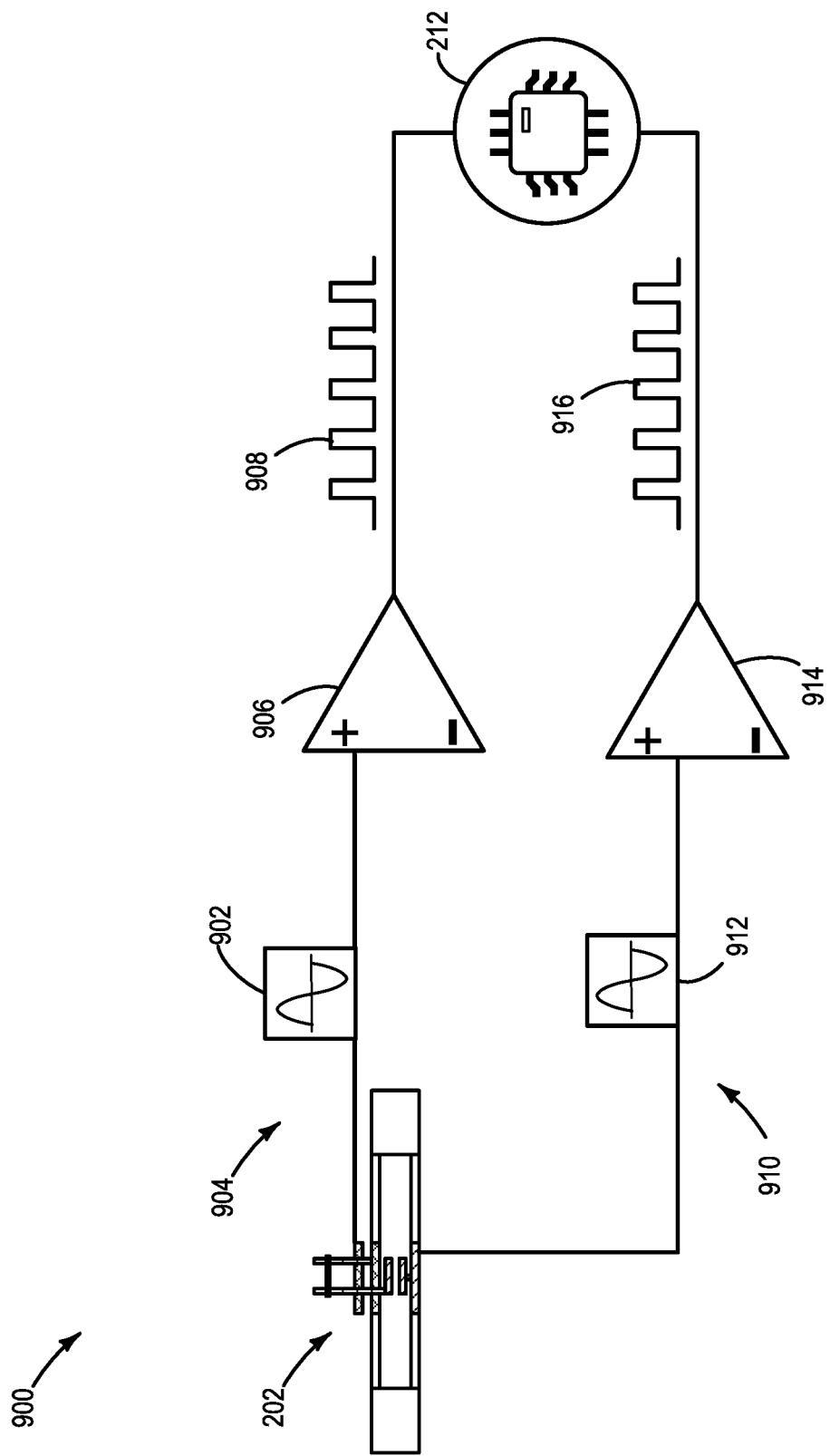
FIG. 9 shows a schematic diagram of signal transmission from an integrated composition-pressure sensor to a controller.

At 618, the method includes determining a fuel pressure of the fuel line between the integrated sensor and the engine via the second section (e.g., the second section 326 of the integrated sensor 202 of FIGS. 3-5, 8) of the integrated sensor comprising the set of plate capacitors. A first plate of the set of plate capacitors may be a first shell of the outer cylinder of the set of cylindrical capacitors and a second plate may be an external plate, with reference to the first shell 320, the second cylinder 312, and the external plate 328 of FIGS. 3-5, and 8. The external plate may be curved to match a curvature of the first shell of the second cylinder or be planar. The external plate may be spaced away from the first shell of the second cylinder by a distance d, as shown in FIG. 8, and the distance when fuel flow through the integrated sensor is low or stationary may be stored in a memory of the controller as a base distance, as well as a capacitance of the second section of the integrated sensor calculated based on the distance.

When fuel flow is slow or stationary, the first shell of the second cylinder may be at the base distance where the first shell is not displaced relative to when fuel pressure rises. The base distance may correspond to a base pressure in the integrated sensor that is also stored in the controller's memory. The increase in fuel pressure may exert an outwards force on the first shell so that the first shell bends slightly outwards or is shifted slight outwards relative to a circumference of the second cylinder. The displacement of the first shell may change the distance between the external plate and the first shell of the second cylinder, thereby varying a potential difference and the capacitance of the set of plate capacitors. The capacitance of the set of plate capacitors may also depend on the fuel permittivity calculated based on the capacitance change at the set of cylindrical capacitors.

The electronic device of the integrated sensor may have a second electrode that is coupled to the set of plate capacitors. At 620, the method includes measuring the capacitance (e.g., capacitance difference) between the set of plate capacitors. In this way, the second electrode may measure the change in capacitance across the set of plate capacitors, which occurs due to a change in pressure of fuel flowing through the sensor. The potential difference across the set of plate capacitors of the integrated sensor may be estimated based on Gauss's law and a Gaussian surface. The calculation is illustrated in a schematic diagram 800, depicting the external plate 328 arranged above the first shell 320 and spaced away by a distance d. A magnetic field flow is formed between the external plate 328 and the first shell 320, as indicated by arrows 802. The potential difference, $\Delta V$, may be determined according to, $$\Delta V = \frac{q}{\epsilon A} d \quad (4)$$

where A is an area of the external plate 328 or the first shell 320 of the second cylinder. The measured capacitance may be related to the permittivity and distance between the plates by the following relationship, $$C = \frac{\epsilon A}{d} \quad (5)$$

where the permittivity, ε, may be the fuel permittivity determined at 612. The measured capacitance of the set of plate capacitors may be relayed to a signal conditions at 622 of the method.

The signal relaying a change in capacitance of the set of plate capacitors may be sent to the signal conditioner to convert the signal to a format readable by the controller. The electronic device of the integrated sensor may relay the capacitance as an electronic signal 912 along a second path 910, shown in the schematic diagram 900 of FIG. 9, to a signal conditioner 912, similar to the signal conditioner 906 in the first path 904. The signal conditioner 914 may also be an amplifier, converting an analog signal from the second section of the integrated composition-pressure sensor 202 to a digital output 916 of the method, resulting in a conversion of the capacitance signal to a voltage output that is sent to the controller at 624.

A change in capacitance, relayed as a voltage, relative to the baseline capacity when fuel is at low flow or stationary within the integrated sensor may be proportional to a change in pressure. The controller may refer to a lookup table stored in the memory controller using the received voltage as an input and a corresponding pressure as an output. The fuel pressure in a flow passage of the integrated sensor is thereby determined at 626.

Figure 10:
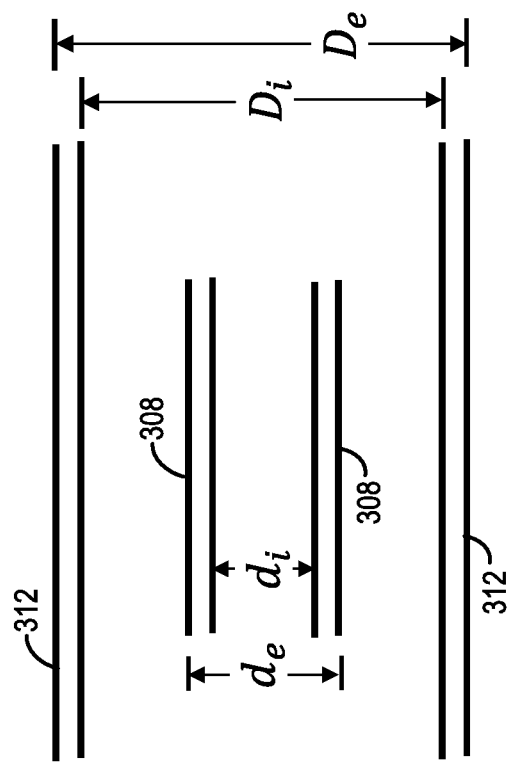
FIG. 10 shows a schematic diagram of a set of cylindrical capacitors and parameters included in a determination of pressure in a fuel line downstream of an integrated composition-pressure sensor.
Figure 10:
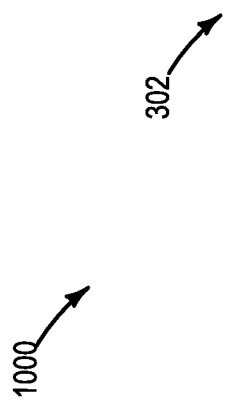

The pressure value may represent a fuel pressure $P_1$ in the integrated sensor, as shown in FIG. 3. However, the positioning of the first cylinder within the path of fuel flow may affect the fuel pressure in the integrated sensor so that the pressure in the integrated sensor is higher than the fuel pressure in the fuel line between the integrated sensor and the engine. Thus, at 628 of the method, the fuel pressure downstream of the integrated sensor may be calculated based on an estimated ring duct friction and volume fuel flow speed of the first cylinder that may be obtained by a fuel delivery module. For example, the downstream pressure, $P_2$, as shown in FIG. 3, may be determined according to, $$P_2 = P_1 + \frac{[0.3164(Re_{D_h})^{-0.25}]\rho L V^2}{2D_h} \quad (6)$$

where Re is Reynolds number, ρ is a density of the fuel, V is the flow speed of the fuel. The hydraulic diameter, $D_h$, in equation 6 may be calculated from inner and outer diameters of the first cylinder 308 and the second cylinder 312, as shown in a schematic diagram 1000 of FIG. 10 depicting the first section 302 of the integrated sensor, based on, $$D_h = \left[\frac{D_i^2 - d_e^2}{D_i + d_e}\right] \quad (7)$$

At 630, the method includes adjusting engine operating parameters, such as spark timing, fuel injection timing, valve timing, and/or exhaust gas recirculation, according to the detected changes in fuel composition and fuel pressure from the integrated sensor. For example, the controller may use the calculated pressure $P_2$ to infer a rail pressure and a fuel flow rate through fuel injectors of the engine, providing the PCM with information to adjust fuel injection accordingly. If fuel pressure is detected to increase, the duration of an injector pulse may be decreased to accommodate the higher flow rate through the fuel injectors. Conversely, a decrease in fuel pressure may result in a longer injector pulse.

In other examples, if the ethanol percentage increases, a spark timing may be advanced due to a higher activation energy of ethanol compared to gasoline and thus a longer ignition period for ethanol. An increase in ethanol content may also reduce a formation of gasoline combustion byproducts such as particulate matter and nitrous oxides and as a result, more gas may be recirculated to the engine intake instead of passing through an after treatment device such as the emission control device 270 of FIG. 2. As another example, opening and closing of intake and exhaust valves at engine cylinders may be timed according to changes in fuel composition to accommodate different periods of time for ignition of the fuel.

In this way, a single integrated sensor, may be used to determine both a fuel composition and a fuel pressure of fuel. The integrated sensor may comprise a set of concentric cylindrical capacitors arranged inline with a fuel line and a set of plate capacitors positioned external to a path of fuel flow, with a common capacitor element shared between the two sets. The capacitance of the set of cylindrical capacitors may be used to estimate a permittivity of the fuel flow from which a percentage of ethanol in the fuel may be calculated. As fuel flows through the set of cylindrical capacitors, pressure from the fuel may displace a shell of an outer cylinder of the set of cylindrical capacitors that is also a plate of the set of plate capacitors. The displacement of the shell of the cylindrical capacitor results in a change in capacitance of the set of capacitor plates which may be translated to a fuel pressure in the integrated sensor. A pressure downstream of the integrated sensor may be calculated based on the fuel pressure in the integrated sensor corrected for an estimated amount of ring duct friction generated by fuel flow through the set of cylindrical capacitors. Thus, the fuel composition and fuel pressure may be determined directly from the integrated sensor and changes to fuel composition and/or pressure may be anticipated before combustion events with the altered composition and/or pressure occur. The integrated sensor may operate independently of other sensing devices and reduce response times to changes in fuel composition and/or fuel pressure, thereby increasing engine performance and decreasing a likelihood of events leading to engine degradation, such as engine knock. Furthermore, by incorporating dual sensing capabilities into one device instead of two, costs and weight of the engine system may be reduced.

The technical effect of configuring a fuel line with an integrated sensor including a set of cylindrical capacitors concentrically arranged and spaced apart from one another, where the set of cylindrical capacitors are adapted to receive a flow of fluid axially through each capacitor of the set of cylindrical capacitors and a set of plate capacitors spaced apart from one another, where a common capacitor element is shared between the set of cylindrical capacitors and set of plate capacitors, is that a number of measuring components (e.g., sensors) is reduced, thereby decreasing engine costs and reducing engine control complexity.

As one embodiment, an integrated fuel composition and pressure sensor includes a set of cylindrical capacitors concentrically arranged and spaced apart from one another, where the set of cylindrical capacitors are adapted to receive a flow of fluid axially through each capacitor of the set of cylindrical capacitors and a set of plate capacitors spaced apart from one another, where a common capacitor element is shared between the set of cylindrical capacitors and set of plate capacitors. In a first example of the sensor, the set of cylindrical capacitors includes an inner cylinder and an outer cylinder, the outer cylinder surrounding the inner cylinder, and wherein the common capacitor element is a portion of the outer cylinder. A second example of the sensor optionally includes the first example, and further includes wherein the set of plate capacitors includes a first plate and a second plate spaced apart from one another, where the first plate is the portion of the outer cylinder and the second plate is positioned outside of the first plate relative to a central axis of the inner cylinder. A third example of the sensor optionally includes one or more of the first and second examples, and further includes, wherein the first plate is adapted to bend and the second plate is static. A fourth example of the sensor optionally includes one or more of the first through third examples, and further includes, wherein a first electrode of an electronic device of the sensor is coupled to the set of cylindrical capacitors and a second electrode of the electronic device is coupled to the set of plate capacitors. A fifth example of the sensor optionally includes one or more of the first through fourth examples, and further includes, wherein the first electrode is adapted to measure of first change in capacitance between the set of cylindrical capacitors that is indicative of a change in fuel composition of fuel flowing through the sensor. A sixth example of the sensor optionally includes one or more of the first through fifth examples, and further includes, wherein the second electrode is adapted to output a second change in capacitance between the set of plate capacitors that is indicative of a change in pressure of fuel flowing through the sensor. A seventh example of the sensor optionally includes one or more of the first through sixth examples, and further includes, wherein the second plate of the set of plate capacitors is arranged parallel to the first plate and parallel to the set of cylindrical capacitors.

As another embodiment, a method includes flowing a fuel through a fuel line and through a sensor arranged in the fuel line, estimating a fuel composition of the fuel from a first signal generated from a change in capacitance between a set of cylindrical capacitors of the sensor which are arranged concentrically with one another and positioned in a flow path of the fuel, and estimating a pressure of the fuel from a second signal generated from a change in capacitance between a set of plate capacitors of the sensor and based on the first signal. In a first example of the method, estimating the fuel composition includes, via a controller adapted to receive the first signal and the second signal from the sensor, calculating a permittivity of the fuel based on the first signal and further comprising, estimating a percentage of ethanol in the fuel from the calculated permittivity. A second example of the method optionally includes the first example, and further includes estimating the pressure of the fuel includes, via the controller, calculating the pressure of fuel based on the second signal and the calculated permittivity, where the change in capacitance between the set of plate capacitors is generated due to a change in distance between plates of the set of plate capacitors. A third example of the method optionally includes one or more of the first and second examples, and further includes, correcting the estimated pressure for an effect of ring duct friction based on a fuel speed and length of the set of the cylindrical capacitors and a density of the fuel to determine a pressure of the fuel in the fuel line, downstream of the sensor and upstream of an engine. A fourth example of the method optionally includes one or more of the first through third examples, and further includes, wherein the set of cylindrical capacitors and the set of plate capacitors share a common element, where the common element is a portion of an outer cylinder that surrounds an inner cylinder of the set of cylindrical capacitors. A fifth example of the method optionally includes one or more of the first through fourth examples, and further includes, wherein flowing fuel through the sensor includes flowing fuel through an interior of the inner cylinder and through a space that separates the inner cylinder and the outer cylinder.

As another embodiment, a fuel system includes a fuel line coupling a fuel tank to an engine, and an integrated sensing device arranged in the fuel line, in line with a path of fuel flow through the fuel line, the device including, a set of cylindrical capacitors formed by concentrically arranged, inner and outer cylindrical capacitors, and a set of plate capacitors formed by a portion of the outer cylindrical capacitor and a static plate arranged outside of the path of fuel flow. In a first example of the fuel system, the inner cylindrical capacitor is arranged entirely within the path of fuel flow. A second example of the fuel system optionally includes the first example, and further includes, wherein, when fuel flows through the fuel line and through the integrated sensing device, fuel flows through an inner passage of the inner cylindrical capacitor formed from an interior of the inner cylindrical capacitor and through an outer passage formed between an outer surface of the inner cylindrical capacitor and an inner surface of the outer cylindrical capacitor. A third example of the fuel system optionally includes one or more of the first and second examples, and further includes, wherein the outer cylindrical capacitor has a first shell and a second shell, each of the first shell and second shell forming a portion of a circumference of the outer cylindrical capacitor. A fourth example of the fuel system optionally includes one or more of the first through third examples, and further includes, wherein the first shell is adapted to outwardly displace, in a direction away from a central axis of the outer cylindrical capacitor, when fuel pressure inside the outer cylindrical capacitor increases. A fifth example of the fuel system optionally includes one or more of the first through fourth examples, and further includes, wherein the first shell of the outer cylindrical capacitor is the portion of the outer cylindrical capacitor that forms a movable plate of the set of plate capacitors and wherein the outward displacement of the first shell changes a distance between the set of plate capacitors.

In another representation, a method includes upon flowing fuel through a device via a fuel line, applying a voltage to the device and determining a composition and pressure of the fuel based on signals relayed by the device. In a first example of the method, flowing fuel through the device includes flowing fuel through inner passages of a set of concentric cylindrical capacitors. A second example of the method optionally includes the first method, and further includes wherein a potential difference is generated between the set of concentric cylindrical capacitors. A third example of the method optionally includes one or more of the first and second examples, and further includes, wherein a capacitance of the set of the concentric cylindrical capacitors is calculated based on the potential difference. A fourth example of the method optionally includes one or more of the first through third examples, and further includes, wherein a permittivity of the fuel flowing through the device and fuel line is determined based on the capacitance of the set of concentric cylindrical capacitors, a length of the set of concentric cylindrical capacitors, and radii of each cylinder of the set of concentric cylindrical capacitors. A fifth example of the method optionally includes one or more of the first through fourth examples, and further includes, wherein the permittivity of the fuel is converted to a fuel composition by a signal converter and relayed to an engine controller. A sixth example of the method optionally includes one or more of the first through fifth examples, and further includes, wherein flowing fuel through the device exerts an outward force on a first shell of an outer cylinder of the set of concentric cylindrical capacitors that is also a first plate of a set of capacitance plates of the device and an external plate is a second plate of the set of capacitance plates. A seventh example of the method optionally includes one or more of the first through sixth examples, and further includes, wherein the outward force on the first plate changes a distance between the first plate and the second plate and also changes a capacitance of the set of capacitance plates. An eighth example of the method optionally includes one or more of the first through seventh examples, and further includes, wherein a capacitance of the set of capacitance plates is calculated based on the distance between the first plate and the second plate, a fuel permittivity determined from the set of concentric cylindrical capacitors, and a surface area of the second plate. A ninth example of the method optionally includes one or more of the first through eighth examples, and further includes, wherein the capacitance of the set of capacitance plates is converted to a fuel pressure by a signal converter and relayed to an engine controller. A tenth example of the method optionally includes one or more of the first through ninth examples, and further includes, wherein the fuel pressure is adjusted to reflect a fuel pressure downstream of the device by calculating an effect of ring duct friction.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. An integrated fuel composition and pressure sensor, comprising:
    a nested set of cylindrical capacitors concentrically arranged and spaced apart from one another, where the nested set of cylindrical capacitors is adapted to receive a flow of fluid axially through each capacitor of the nested set of cylindrical capacitors;
    wherein the set of cylindrical capacitors includes an inner cylinder and an outer cylinder, the outer cylinder surrounding the inner cylinder, and wherein a portion of the outer cylinder is a common capacitor element; and
    a plate capacitor forming a set with the common capacitor element, wherein the common capacitor element is shared between the nested set of cylindrical capacitors and the plate capacitor set.

2. The integrated fuel composition and pressure sensor of claim 1, wherein the plate capacitor set includes the common capacitor element and a plate spaced apart from one another, wherein the plate is positioned outside of the common capacitor element relative to a central axis of the inner cylinder.

3. The integrated fuel composition and pressure sensor of claim 2, wherein the common capacitor element is adapted to bend and the plate is static.

4. The integrated fuel composition and pressure sensor of claim 3, wherein a first electrode of an electronic device of the sensor is coupled to the nested set of cylindrical capacitors and a second electrode of the electronic device is coupled to the plate capacitor and the common capacitor element.

5. The integrated fuel composition and pressure sensor of claim 4, wherein the first electrode is adapted to measure a first change in capacitance between the nested set of cylindrical capacitors that is indicative of a change in fuel composition of fuel flowing through the sensor.

6. The integrated fuel composition and pressure sensor of claim 4, wherein the second electrode is adapted to measure a second change in capacitance between the plate capacitor and the common capacitor element that is indicative of a change in pressure of fuel flowing through the sensor.

7. The integrated fuel composition and pressure sensor of claim 2, wherein the plate capacitor is arranged parallel to the common capacitor element and parallel to the nested set of cylindrical capacitors comprising the common capacitor element.

8. A method, comprising;
    flowing a fuel through a fuel line and through a sensor arranged in the fuel line;
    estimating a fuel composition of the fuel from a first signal generated from a change in capacitance between a nested set of cylindrical capacitors of the sensor which are arranged concentrically with one another and positioned in a flow path of the fuel, wherein the nested set of cylindrical capacitors includes an inner cylinder and an outer cylinder, the outer cylinder surrounding the inner cylinder, and wherein a common capacitor element is a portion of the outer cylinder; and estimating a pressure of the fuel from a second signal generated from a second change in capacitance between a plate capacitor and the common capacitor element and based on the first signal.

9. The method of claim 8, wherein estimating the fuel composition includes, via a controller adapted to receive the first signal and the second signal from the sensor, calculating a permittivity of the fuel based on the first signal, and further comprising estimating a percentage of ethanol in the fuel from the calculated permittivity.

10. The method of claim 9, wherein estimating the pressure of the fuel includes, via the controller, calculating the pressure of fuel based on the second signal and the calculated permittivity, wherein the second change in capacitance between the plate capacitor and the common capacitor element is generated due to a change in distance between the plate capacitor and the common capacitor element.

11. The method of claim 8, further comprising correcting the estimated pressure of the fuel for an effect of ring duct friction based on a fuel speeds a length of the nested set of the cylindrical capacitors and a density of the fuel to determine a pressure of the fuel in the fuel line, downstream of the sensor and upstream of an engine.

12. The method of claim 8, wherein flowing fuel through the sensor includes flowing fuel through an interior of the inner cylinder and through a space that separates the inner cylinder and the outer cylinder.

13. A fuel system, comprising:
a fuel line coupling a fuel tank to an engine; and
an integrated sensing device arranged in the fuel line, in line with a path of fuel flow through the fuel line, the device including:
  a nested set of cylindrical capacitors formed by concentrically arranged, inner and outer cylindrical capacitors, the outer cylindrical capacitor surrounding the inner cylindrical capacitor; and
  a static plate capacitor arranged outside of the path of fuel flow and forming a static plate capacitor set with a portion of the outer cylindrical capacitor.

14. The fuel system of claim 13, wherein the inner cylindrical capacitor is arranged entirely within the path of fuel flow.

15. The fuel system of claim 14, wherein, when fuel flows through the fuel line and through the integrated sensing device, fuel flows through an inner passage of the inner cylindrical capacitor formed from an interior of the inner cylindrical capacitor and through an outer passage formed between an outer surface of the inner cylindrical capacitor and an inner surface of the outer cylindrical capacitor.

16. The engine system of claim 13, wherein the outer cylindrical capacitor has a first shell and a second shell, each of the first shell and the second shell forming a portion of a circumference of the outer cylindrical capacitor.

17. The engine system of claim 16, wherein the first shell is adapted to outwardly displace, in a direction away from a central axis of the outer cylindrical capacitor, when fuel pressure inside the outer cylindrical capacitor increases.

18. The engine system of claim 16, wherein the first shell of the outer cylindrical capacitor is the portion of the outer cylindrical capacitor that forms a movable plate of the static plate capacitor set, and wherein the outward displacement of the first shell changes a distance between the portion of the outer cylindrical capacitor and the static plate capacitor.

* * * * *